United States Patent
Rao et al.

(10) Patent No.: US 6,967,202 B2
(45) Date of Patent: Nov. 22, 2005

(54) METHOD OF SYNTHESIZING DIKETOPIPERAZINES

(75) Inventors: Nagaraja K. R. Rao, Wales (GB); Stephen Turner, Bracknell (GB)

(73) Assignee: DMI Biosciences, Inc., Englewood, CO (US)

( * ) Notice: Subject to any disclaimer, the term of this patent is extended or adjusted under 35 U.S.C. 154(b) by 353 days.

(21) Appl. No.: 09/922,604

(22) Filed: Aug. 2, 2001

(65) Prior Publication Data

US 2002/0038026 A1 Mar. 28, 2002

Related U.S. Application Data

(60) Provisional application No. 60/223,075, filed on Aug. 4, 2000.

(51) Int. Cl.⁷ .......................................... A61K 31/4965
(52) U.S. Cl. ..................... 514/255.02; 514/19; 530/331
(58) Field of Search .............................. 514/255.02, 19; 530/331

(56) References Cited

U.S. PATENT DOCUMENTS

| | | | |
|---|---|---|---|
| 3,928,330 A | 12/1975 | Ramey et al. | 260/242 |
| 4,289,759 A | 9/1981 | Heavner et al. | 424/177 |
| 4,312,987 A | 1/1982 | Beck | 544/346 |
| 4,331,595 A | 5/1982 | Heavner et al. | 260/112.5 |
| 4,694,061 A | 9/1987 | Pfeifer | 544/385 |
| 4,940,709 A | 7/1990 | Shimazaki et al. | 514/253 |
| 4,992,552 A | 2/1991 | Hubbs et al. | 544/385 |
| 5,047,401 A | 9/1991 | Lipsky et al. | 514/19 |
| 5,817,751 A | 10/1998 | Szardenings et al. | 530/317 |
| 5,932,579 A | 8/1999 | Campbell et al. | 514/249 |
| 5,990,112 A | 11/1999 | Campbell et al. | 514/255 |
| 6,555,543 B2 * | 4/2003 | Bar-Or et al. | 514/255.02 |

FOREIGN PATENT DOCUMENTS

| | | |
|---|---|---|
| EP | 0 043 219 B1 | 10/1983 |
| EP | 0 216 746 B1 | 10/1990 |
| EP | 0 493 812 A1 | 7/1992 |
| WO | WO 91/14378 | 10/1991 |
| WO | WO 96/00391 | 1/1996 |
| WO | WO 97/36888 | 10/1997 |
| WO | WO 99/40931 | 8/1999 |

OTHER PUBLICATIONS

Shimazaki (J Med Chem 30, 1706–1709, 1987).*
English Abstract of JP–3176478.*
English Abstract of JP–63290868.*
Nitecki et al., *J. Org. Chem.*, 33(2):864–866 (1968).
Shimazaki et al., *Chem. Pharm. Bull.*, 35:3527–3530 (1987).
Shimazaki et al., *J. Med. Chem.*, 30:1709–1711 (1987).
Shimazaki et al., *Lipids*, 26(12):1175–1178 (1991).
Smith et al., *Bioorg. Med. Chem.*, 8:2369–2374 (1998).
Yoshida et al., *Prog. Biochem. Pharmacol.*, 22:66–80 (1988).

* cited by examiner

*Primary Examiner*—David Lukton
(74) *Attorney, Agent, or Firm*—Sheridan Ross P.C.

(57) ABSTRACT

The invention provides a method of synthesizing a diketopiperazine of the formula:

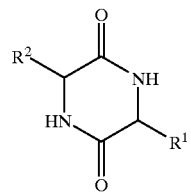

wherein:

$R^1$ is —$CH_2COR^3$, or —$CH_2CH_2COR^3$;

$R^2$ is the side chain of an amino acid selected from the group consisting of glycine, alanine, valine, leucine, isoleucine, serine, threonine, aspartic acid, asparagine, glutamic acid, glutamine, lysine, hydroxylysine, histidine, arginine, phenylalanine, tyrosine, tryptophan, thyroxine, cysteine, methionine, norvaline and ornithine;

$R^3$ is —OH, —$NH_2$, —$OR^4$, —$NHR^4$, or —$NR^4R^4$; and each $R^4$ is independently an alkyl, aryl, alkylaryl, or arylalkyl.

8 Claims, No Drawings

METHOD OF SYNTHESIZING DIKETOPIPERAZINES

This application claims benefit of provisional application 60/223,075 filed Aug. 4, 2000.

FIELD OF THE INVENTION

This invention relates to a method of synthesizing diketopiperazines.

BACKGROUND

Many diketopiperazines of the general formula (1) are known to possess

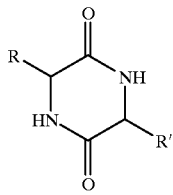

(1)

pharmacological and other biological activities, and libraries of such compounds have been synthesized to identify other diketopiperazines having beneficial biological and medicinal activities. See, e,g., Smith et al., *Bioorg. Med. Chem Letters*, 8:2369–2374 (1998); Nitecki et al., *J. Org. Chem.*, 33:864–866 (1968); U.S. Pat. No. 5,817,751; and PCT application WO 96/00391. Diketopiperazines of formula (1) have been synthesized by a variety of methods, but, a thermal cyclization of the corresponding dipeptide to produce the cyclic product seems to be the method of choice because of its simplicity. In addition, the method is known to produce sterically-pure product (Nitecki et al., *J. Org. Chem.*, 33:864–866 (1968)).

However, several groups of workers have encountered difficulty in employing the thermal cyclization method to synthesize diketopiperazines containing an aspartic acid residue. The inability of the dipeptide to form a cyclic product has been attributed to the presence of the free β carboxyl group of the aspartic acid. Similar difficulties would be expected synthesizing diketopiperazines containing a glutamic acid. Consequently, a new strategy to synthesize diketopiperazines wherein one of the amino acid is aspartic acid or glutamic acid is needed.

SUMMARY OF THE INVENTION

The present invention provides the needed method. In particular, the invention provides a method of synthesizing diketopiperazines of the following formula:

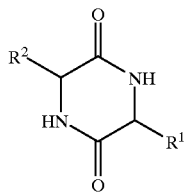

(2)

wherein:
$R^1$ is —$CH_2COR^3$, or —$CH_2CH_2COR^3$;
$R^2$ is the side chain of an amino acid selected from the group consisting of glycine, alanine, valine, leucine, isoleucine, serine, threonine, aspartic acid, asparagine, glutamic acid, glutamine, lysine, hydroxylysine, histidine, arginine, phenylalanine, tyrosine, tryptophan, thyroxine, cysteine, methionine, norvaline and ornithine;
$R^3$ is —OH, —$NH_2$, —$OR^4$, —$NHR^4$, or —$NR^4R^4$; and each $R^4$ is independently an alkyl, aryl, alkylaryl, or arylalkyl.

The method comprises providing a first amino acid selected from the group consisting of glycine, alanine, valine, leucine, isoleucine, serine, threonine, aspartic acid, asparagine, glutamic acid, glutamine, lysine, hydroxylysine, histidine, arginine, phenylalanine, tyrosine, tryptophan, thyroxine, cysteine, methionine, norvaline and ornithine. The first amino acid is optionally protected with one or more protecting groups so as to prevent unwanted side reactions.

The first amino acid is reacted with a second amino acid derivative which is either an aspartic acid derivative of the following formula $NH_2CH(CH_2COOR^5)COOH$, or a glutamic acid derivative of the following formula $NH_2CH(CH_2CH_2COOR^5)COOH$, wherein $R^5$ is a lower alkyl or alkylaryl. The amino group or α carboxyl group of the second amino acid derivative is optionally protected with a protecting group so as to prevent unwanted side reactions. The reaction of the first amino acid and the second amino acid derivative takes place under conditions effective to form a dipeptide.

The resulting dipeptide is then cyclized to form a diketopiperazine having the formula:

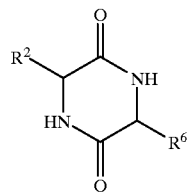

wherein:
$R^6$ is —$CH_2COOR^5$, or —$CH_2CH_2COOR^5$.

Then, the $R^5$ group is removed from the diketopiperazine to give a compound of formula 2 wherein $R^3$ is —OH. Diketopiperazines of formula 2 wherein $R^3$ is other than —OH (i.e., amides and esters) may be made from this diketopiperzine.

DETAILED DESCRIPTION OF THE PRESENTLY PREFERRED EMBODIMENTS OF THE INVENTION

The present invention provides a method of synthesizing diketopiperazines of the following formula:

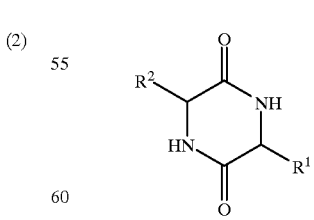

(2)

wherein:
$R^1$ is —$CH_2COR^3$, or —$CH_2CH_2COR^3$;
$R^2$ is the side chain of an amino acid selected from the group consisting of glycine, alanine, valine, leucine, isoleucine, serine, threonine, aspartic acid, asparagine, glutamic acid, glutamine, lysine, hydroxylysine, histidine, arginine, phenylalanine, tyrosine, tryptophan, thyroxine, cysteine, methionine, norvaline and ornithine;

$R^3$ is —OH, —NH$_2$, —OR$^4$, —NHR$^4$, or —NR$^4$R$^4$; and each R$^4$ is independently an alkyl, aryl, alkylaryl, or arylalkyl.

By "side chain" of an amino acid is meant that portion of the amino acid attached to the common

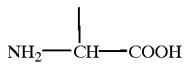

backbone of all of the amino acids listed above. For instance, the side chain of glycine is —H, the side chain of alanine is —CH$_3$, and the side chain of serine is —CH$_2$OH.

By "alkyl" is meant a straight-chain or branched-chain alkyl containing 1–30 carbon atoms, preferably 1–18 carbon atoms. "Lower alkyl" means a straight-chain or branched chain alkyl containing 1–6 carbon atoms.

By "aryl" is meant an aromatic group having at least one aromatic ring (e.g., phenyl).

By "alkylaryl" is meant a lower alkyl having attached thereto an aryl (e.g., —CH$_2$C$_6$H$_5$ or —CH$_2$CH(C$_6$H$_5$)CH$_3$).

By "arylalkyl" is meant an aryl having attached thereto a lower alkyl (e.g., —C$_6$H$_4$—CH$_3$).

The synthesis of the diketopiperazines utilizes standard solution-phase or solid-phase peptide synthetic methods which are well known in the art. Preferably, the synthesis of the diketopiperazines utilizes solid-phase peptide synthetic methods.

The first step of the method of the invention comprises providing a first amino acid. The first amino acid is selected from the group consisting of glycine, alanine, valine, leucine, isoleucine, serine, threonine, aspartic acid, asparagine, glutamic acid, glutamine, lysine, hydroxylysine, histidine, arginine, phenylalanine, tyrosine, tryptophan, thyroxine, cysteine, methionine, norvaline and ornithine. These amino acids, which may be in their D- or L-enantiomeric form, are commercially available or can be made by methods well known in the art (see, e.g., Williams, *Synthesis Of Optically Active α-Amino Acids* (Pergammon Press, 1989)).

The first amino acid is also preferably protected with one or more protecting groups to prevent unwanted side reactions during the synthesis. Such protecting groups, and methods for attaching and removing them, are well known in the art. See, e.g., Green and Wuts, *Protective Groups In Organic Chemistry (Wiley* 1992) and Grant, *Synthetic Peptides: A User's Guide* (Freemen 1992).

The first amino acid is reacted with an aspartic acid derivative of the following formula NH$_2$CH(CH$_2$COOR$^5$)COOH or a glutamic acid derivative of the following formula NH$_2$CH(CH$_2$CH$_2$COOR$^5$)COOH, wherein R$^5$ is a lower alkyl or alkylaryl. Preferably R$^5$ is benzyl (—CH$_2$C$_6$H$_5$; Bz). The benzyl group has been found not only to protect the side-chain carboxyls of these amino acids, but also to facilitate cyclization of the dipeptide. Furthermore, the benzyl can be removed from the dipeptide under neutral conditions which prevents racemization of the chiral center (carbons bearing the R$^1$ and R$^2$ groups).

The aspartic and glutamic acid derivatives NH$_2$CH(CH$_2$COOR$^5$)COOH and NH$_2$CH(CH$_2$CH$_2$COOR$^5$)COOH are commercially available or may be prepared by known methods (see, e.g., Bodansky and Bodansky, *The Practice of Peptide Synthesis*, pages 63–66 (2nd ed., Springer-Verlag, 1994). The amino group or the a carboxyl of the aspartic and glutamic acid derivatives can optionally be blocked with a standard protecting group (see above) in order to prevent unwanted side reactions.

As noted above, the synthesis of the diketopiperazines preferably utilizes solid-phase peptide synthetic methods. The first amino acid or the aspartic or glutamic acid derivative is attached to a solid support through its α carboxyl for solid-phase synthesis. The solid support may be any solid support which is compatible with peptide synthesis, such as those described in Grant and Atherton, *Solid Phase Peptide Synthesis: A Practical Approach* (IRL Press 1989). Suitable solid supports are available commercially or can be prepared by standard methods. See PCT application WO 96/00391. The solid support may contain linker or spacer molecules which anchor the first amino acid or the aspartic acid or glutamic acid derivative to the support surface. A variety of linkers with different properties are well known in the art. See, e.g., Grant, *Synthetic Peptides: A User's Guide* (Freemen 1992) and PCT application WO 96/00391. The linker will typically include a functional group to which the first amino acid or the aspartic acid or glutamic acid derivative is attached.

Preferably, the first amino acid is attached to the solid support and, prior to coupling the aspartic acid or glutamic acid derivative to the first amino acid, the protecting group, if present, on the a amino group of the bound first amino acid is removed. The removal of the protecting group of any side-chain amino groups should be avoided, however, so conditions must be chosen to deprotect the α amino group without deprotecting any side chain amino groups. Suitable deprotection conditions are known in the art. For example, removal of 9-fluorenylmethyloxycarbonyl may be performed with 20% to 55% of a secondary amine base, such as piperidine, in a polar, aprotic solvent, such as dimethylformamide, methylene chloride or N-methylpyrrolidine. Diisopropyl silane is preferably added to prevent trans-esterification during deprotection, which can be pronounced in large scale preparations.

The reaction between the first amino acid and the aspartic or glutamic acid derivative takes place under conditions effective to produce a peptide bond so that a dipeptide is formed. These conditions are well known in the art. For instance, a coupling catalyst (such as 2-(1H-benzotriazole-1-yl)-1,2,3,3-tetramethyluroniumtetrafluoroborate, benzotriazole-1-yl-oxytris(dimethylamino)phosphonium hexafluorophospate, 2-(1H-benzotriazole-1-yl)-1,1,3,3-tetramethyluroniumhexaphosphate, 1-hydroxybenzotriazole, diisopropylamine, dicyclohexylcarbodiimide, ) may be used to effect formation of the dipeptide. Typically, an excess of the coupling catalyst is used, with quantities ranging from 2 to 10 equivalents or more. Often the degree of excess is determined with respect to the reactivity of the chemical species being coupled. Polar, aprotic solvents (such as dimethylformamide, N-methylpyrollidine, methylene chloride and dimethylsulfoxide) are preferred. Reaction times may vary from one-half hour to overnight, and temperatures may vary from room temperature to reflux.

Next, if the dipeptide is bound to a solid support, it is removed from the solid support using standard procedures well known in the art. The conditions effective to remove the dipeptide from the solid support will be depend on the solid support and linker chosen. Generally, the peptide will be removed by acid hydrolysis using a strong acid, such as trifluoroacetic acid.

The dipeptide is then cyclized to form a diketopiperazine; this diketopiperazine will have the side-chain carboxyl of the aspartic acid or glutamic acid derivative still in the ester form. Cyclization is accomplished by heating the dipeptide under neutral conditions. Typically, the dipeptide will be heated at from about 80° C. to about 180° C., preferably at about 120° C. The solvent will be a neutral solvent. For instance, the solvent may comprise an alcohol (such as butanol, methanol, ethanol, and higher alcohols, but not phenol) and an azeotropic co-solvent (such as toluene, benzene, or xylene). Preferably, the alcohol is butan-2-ol, and the azeotropic co-solvent is toluene. The heating is continued until the reaction is complete, and such times can be determined empirically. Typically, the dipeptide will be cyclized by refluxing it for about 8–24 hours, preferably about 18 hours.

Finally, the $R^5$ group is removed from the diketopiperazine by methods well known in the art for removing protecting groups (see above). Preferably, when the $R^5$ group is benzyl, it is removed from the diketopiperazine by hydrogenation using a palladium on carbon catalyst (Pd/C). The use of strong acids (mineral acids, such as sulfuric or hydrochloric acids), strong bases (alkaline bases, such as potassium hydroxide or sodium hydroxide), and strong reducing agents (e.g., lithium aluminum hydride) should be avoided in order to maintain the chirality of the final compound.

Attempts to prepare Asp-Ala diketopiperazine (5) using prior art methods failed to give the desired product. In particular, literature procedures describing the synthesis of (5) from formate salts of dipeptides failed to give any product when the side chain contained a free carboxylic acid. By contrast, use of the method of the present invention gives the desired diketopiperazines. When $R^5$ is benzyl, yields of about 90% with a purity greater than 95% are obtained. Further, the benzyl esters of the dipeptides are easily isolated from the reaction medium and are easily purified by crystallization which, in turn, lends itself to obtaining an optically pure product.

Once the $R^5$ group has been removed, the free acid can be derivatized, if desired, to form standard derivatives, such as amides and esters. Methods which can be used to convert the free acid to an amide or ester are well known in the art.

The diketopiperazines of formula (2) have been found to inhibit the effects of platelet activating factor (PAF). See co-pending provisional application 60/222,849, filed Aug. 4, 2000, the complete disclosure of which is incorporated herein by reference. For instance, a disease or condition mediated by PAF can be treated, platelet aggregation can be inhibited, the production and/or release of interleukin 8 (IL-8) by cells can be inhibited, and a disease or condition mediated by IL-8 can be treated with diketopiperazines of formula (2). Diseases or conditions mediated by PAF include acute respiratory distress syndrome, allergies, arthritis, asthma, autoimmune diseases, bronchitis, cardiovascular disease, Crohn's disease, cystic fibrosis, emphysema, gastrointestinal ulceration, inflammation, inflammatory bowel disease, ischemia, multiple organ dysfunction syndrome, myocardial infarction, neoplastic diseases, ophthalmic inflammation, pain, psoriasis, respiratory infections, sepsis, shock and ulcerative colitis, and any of these diseases or conditions can be treated with diketopiperazines of formula (2). Diseases or conditions mediated by IL-8 include acute respiratory distress syndrome, allergies, arthritis, asthma, autoimmune diseases, bronchitis, cancer, Crohn's disease, cystic fibrosis, emphysema, endocarditis, gastritis, inflammatory bowel disease, ischemia reperfusion, multiple organ dysfunction syndrome, neoplastic diseases, nephritis, pancreatitis, respiratory viral infections, sepsis, shock, ulcerative colitis, and other inflammatory disorders, and any of these diseases or conditions can also be treated with diketopiperazines of formula (2).

EXAMPLES

Example 1

Synthesis of Asp-Ala Diketopiperazine (5)

Wang resin having 9-fluorenylmethyloxycarbonyl-protected alanine (Ala-Fmoc) attached thereto (3 grams (g), 2.52 mmol, 1 equivalent, NovaBiochem™, La Jolla, Calif.) was transferred to a clean round-bottom, 100 mL flask, and a solution of piperidine (12 mL) in dimethylformamide (DMF; 18 mL) was added to the resin in the flask. The solution was swirled for 1 hour, and the resin was isolated in a sintered glass funnel. The resin was washed with DMF (3×30 mL) followed by dichloromethane (DCM; 3×30 mL) and allowed to dry under vacuum for 5 minutes. Preferred protecting groups are 9-fluorenylmethyloxycarbonyl (Fmoc) and t-butoxycarbonyl (Boc).

The partially-dried resin was transferred into a clean round-bottom, 100 mL flask, and DMF (10 mL) was added. Then, Boc-Asp(OBz)OH (3.25 g,10.07 mmol, 4 equivalents; Aldrich™) was added, followed by diisopropylamine (2.83 mL, 2.04 g, 20.19 mmol, 8 equivalents) and 2-(1H-benzotriazole-1-yl)-1,2,3,3-tetramethyluroniumtetrafluoroborate (TBTU; 3.24 g, 10.09 mmol, 4 equivalents, Acros, Loughborough Leicestershire, UK). The slurry was allowed to react under anaerobic conditions over 12 hours. At the end of this time, the resin showed a negative ninhydrin test, indicating the completion of the coupling reaction. The resin was vacuum filtered and washed with DMF (3×30 mL) followed by DCM (3×30 mL). The resin was allowed to dry at room temperature under vacuum for 10 minutes before transferring it into a clean round-bottom,100 mL flask.

Trifluoroacetic acid (TFA; 16.5 mL) was added to the dried resin and, upon its addition, the resin turned a red color. After swirling the resin for a further 30 minutes, TFA was removed by filtration, and the resin was washed with DCM (4×20 mL). The organic components were pooled, and toluene (20 mL) was added. The combined organic materials were evaporated to dryness under vacuum. Traces of TFA were removed by the addition of toluene and evaporation. The process was repeated until all TFA had been removed. This procedure resulted in a product as a pale yellow oil whose NMR and mass spectrophotometric data were consistent with the expected dipeptide benzyl ester whose structure (3) is shown below.

The dipeptide 3 was dissolved in butan-2-ol (40 mL) and diluted with toluene (60 mL). This solution was allowed to reflux for 24 hours. At the end of this period, the solution was allowed to cool to room temperature. It was then concentrated on a rotary evaporator, while maintaining the temperature at 50° C. Upon concentration, a white solid precipitated, and the precipitate was removed by filtration. The precipitate was washed with toluene (10 mL) and dried. The residue (0.650 g) gave a negative ninhydrin test. It was, then, crystallized from hot methanol. The spectroscopic and analytical results for the crystallized product confirmed its structure to be the desired compound—Asp-Ala diketopiperazine-benzyl ester shown below (4).

This compound (400 mg) was dissolved in methanol (250 mL), and palladium on carbon catalyst (Pd/C; 10%, 0.4 g; Fluka™ Chemicals, Dorset UK) was added carefully. The flask was purged with hydrogen and kept at a positive hydrogen pressure. The solution was kept in this atmosphere for at least 4 hours. The catalyst was removed with a filtering aid (celite) and washed with methanol. The methanol washings were combined, and the solvent was removed (yield 200 mg). Mass spectrometer and NMR analysis showed that the free acid Asp-Ala diketopiperazine (3-methyl-2,5-diketopiperazine-6-acetic acid, 5) had formed without any cross contamination.

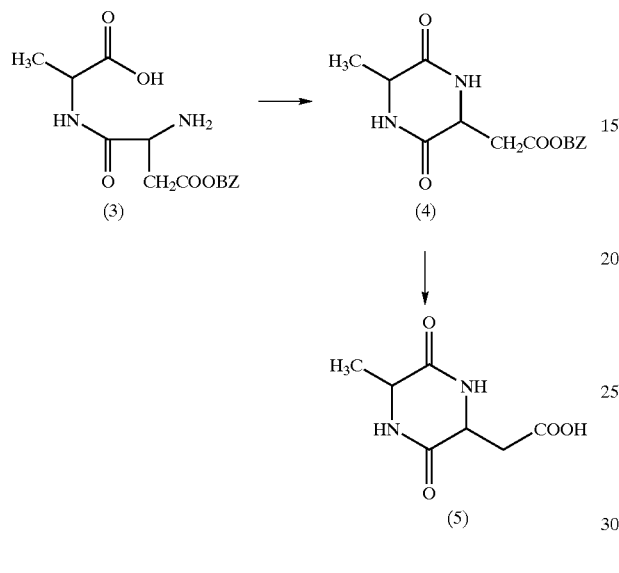

Example 2

Preparation Of Asp-Ala Diketopiperazine Amide (6)

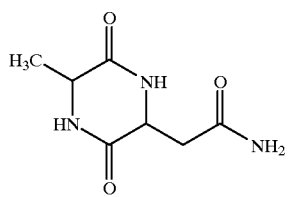

To a solution of 3-methyl-2,5-diketopiperazine-6-acetic acid (0.151 g, 0.81 mmol, 1 equivalent, preparation described in Example 1, 5) in DMF (2.5 mL) was added carbonyl diimidazole (0.26 g, 1.60 mmol, 2 equivalents, Aldrich™ Chemical Co., Milwaukee, Wis.). After stirring at room temperature for 1 hour, solid ammonium acetate (0.63 g, 8.17 mmol, 10 equivalents, Aldrich™) was added. Stirring at room temperature was continued overnight, at which time the reaction was partitioned between water (20 mL) and ethyl acetate (10 mL). The aqueous layer was washed with a second aliquot of ethyl acetate (10 mL), and it was then evaporated to dryness under reduced pressure (61° C.). Traces of DMF were removed by further co-evaporations with water and then toluene to give a white solid (362 mg). This was taken up into a minimum volume of methanol in DCM (20:80 v/v) and flushed through a silica plug (10 g, chromatography grade silica; Aldrich) using methanol in DCM (20:80 v/v). The solvent eluted was fractionated, and the appropriate fractions were pooled and evaporated under reduced pressure (40° C.) to give a white solid. The product was then recrystallized from methanol to given the desired product (0.116 g, 76% yield, 6).

Example 3

Alternate Syntheses of Asp-Ala Diketopiperazine

Essentially there are two ways that Asp-Ala diketopiperazine could be prepared, and the two processes are shown schematically below.

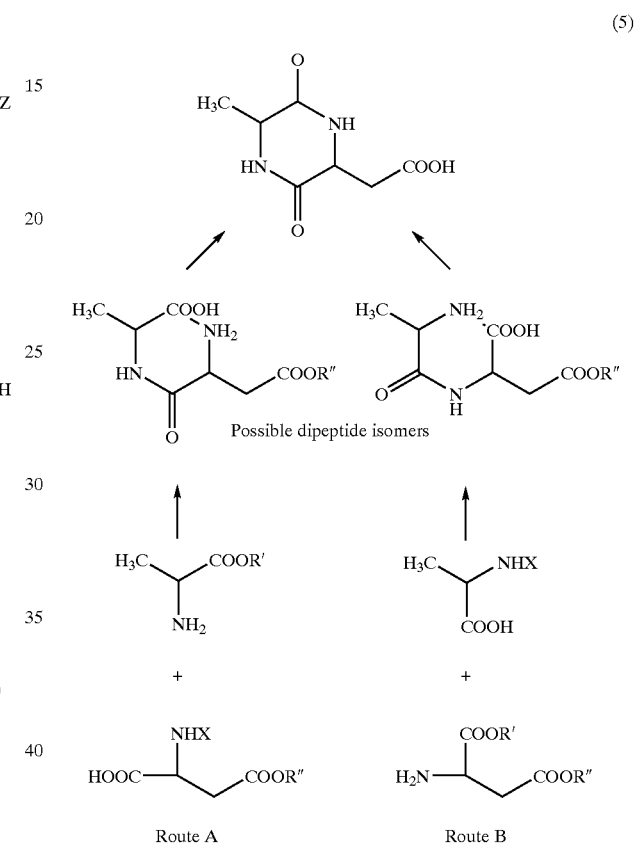

In this diagram, R', R", and X are protecting groups.

In Route A, the free α-carboxyl of the alanine is capable of undergoing an intramolecular cyclization with the free amino functional group of the protected aspartic acid. Route B describes the other alternative, whereby the free amino moiety of alanine cyclizes with the free carboxyl of the C-protected aspartic acid.

Solid phase synthesis (resin), as well as solution phase peptide chemistry, will give the dipeptide isomers, and both of these will yield the Asp-Ala diketopiperazine (5) upon cyclization. The method described in Example 1 is a Route A synthesis. Asp-Ala diketopiperazine has also been synthesized by Route B, and the spectrometric and chromatographic behaviors of the Asp-Ala diketopiperazine synthesized by the two Routes are identical.

The method described in Example 1 (Route A) is preferred for several reasons. The Fmoc-protected, resin-bound alanine is easily synthesized and commercially available on a large scale. Thus, this procedure could easily be scaled up. Also, the overall production cost of Route A is very much lower than that of Route B.

Example 4

Preparation of Glu-Ala Diketopiperazine

Wang resin having Ala-Fmoc attached thereto (3 g, 2.52 mmol, 1 equivalent, NovaBiochem™) was transferred to a clean round-bottom, 100 mL flask, and a solution of piperidine (12 mL) in DMF (18 mL) was added to the resin in the flask. The solution was swirled for 1 hour, and the resin was isolated in a sintered glass funnel. The resin was washed with DMF (3×30 mL) followed by DCM (3×30 mL) and allowed to dry under vacuum for 5 minutes. Preferred protecting groups are 9-fluorenylmethyloxycarbonyl (Fmoc) and t-butoxycarbonyl (Boc).

The partially dried resin was transferred into a clean round-bottom 100 ml flask and DMF (10 mL) was added. Then Boc-Glu(OBz)OH (3.40 g, 10.08 mmol, 4 equivalents, Sigma™, St. Louis, Mo.) was added, followed by diisopropylamine (2.83 mL, 2.04 g, 20.19 mmol, 8 equivalents, Aldrich) and TBTU (3.24 g, 10.09 mmol, 4 equivalents, Acros). The slurry was allowed to react under anaerobic conditions for 10 hours. At the end of this time, the resin showed a negative ninhydrin test, indicating the completion of the coupling reaction. The resin was vacuum filtered and washed with DMF (3×30 mL) followed by DCM (3×30 mL). The resin was allowed to air dry at room temperature under vacuum for 10 minutes before transferring it into a clean round-bottom 100 mL flask.

TFA (16.5 mL) was added to the dried resin and, upon its addition, the resin turned a red color. After swirling the resin for a further 30 minutes, TFA was removed by filtration, and the resin was washed with DCM (4×20 mL). The organic components were pooled, and the combined organic materials were evaporated to a pale yellow paste under vacuum. Traces of TFA were removed by the addition of toluene and evaporation. The process was repeated until all TFA had been removed. This procedure resulted in a product as a pale yellow residue whose NMR and mass spectrophotometic data were consistent with the expected dipeptide benzyl ester whose structure (7) is shown below.

The dipeptide 7 was dissolved in butan-2-ol (40 mL) and diluted with toluene (60 mL). This solution was allowed to reflux for 18 hours. At the end of this period, the solution was allowed to cool to room temperature. It was then concentrated on a rotary evaporator while maintaining the temperature at 50° C. Upon concentration, a white solid was formed, and the precipitate was removed by filtration. The precipitate was washed with toluene (10 mL) and dried. The residue (0.683 g) gave a negative ninhydrin test. It was then crystallized from hot methanol. The spectroscopic and analytical results for the crystallized product confirmed its structure to be the desired compound—Glu-Ala-diketopiperazine-benzyl ester shown below (8).

This compound (500 mg) was dissolved in methanol (400 mL), and Pd/C (10%, 0.5 g) was added carefully. The flask was purged with hydrogen and kept at a positive hydrogen pressure. The solution was kept in this atmosphere for at least 7 hours. The catalyst was removed with a filtering aid (celite) and washed with methanol. The methanol washings were combined and the solvent was removed (yield 200 mg). Mass spectrometer and NMR analysis showed that the free acid Glu-Ala diketopiperazine (3-methyl-2,5-diketopiperazine-7-acetic acid; 9) had formed without any cross contamination.

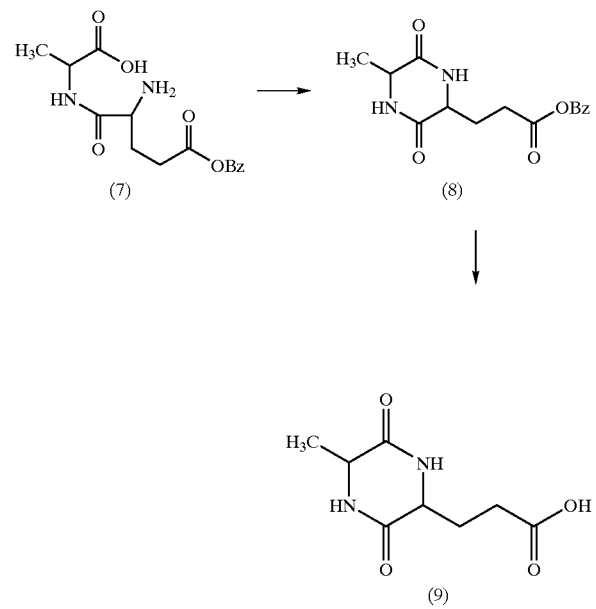

Example 5

Preparation of Glu-Ala Diketopiperazine Amide

To a solution of 3-methyl-2,5-diketopiperazine-7-acetic acid (0.153 g, 0.75 mmol, 1 equivalent, preparation described in Example 4, 9) in DMF (2.5 ml) was added carbonyl diimidazole (0.24 g, 1.48 mmol, 2 equivalents, Aldrich™). After stirring at room temperature for 1 hour, solid ammonium acetate (0.58 g, 7.52 mmol, equivalents, Aldrich) was added. Stirring at room temperature was continued overnight, at which time the reaction was partitioned between water (20 ml) and ethyl acetate (10 ml). The aqueous layer was washed with a second aliquot of ethyl acetate (10 ml), and it was then evaporated to dryness under reduced pressure (56° C.). Traces of DMF were removed by further co-evaporations with water and then toluene to give a white solid (317 mg). This was taken up into a minimum volume of methanol in DCM (20:80 v/v) and flushed through a silica plug using methanol in DCM (20:80 v/v). The solvent eluted was fractionated, and the appropriate fractions were pooled and evaporated under reduced pressure (40° C.) to give a white solid. The product was then recrystallized from methanol to give the desired product 10 (0.086 g, 57%).

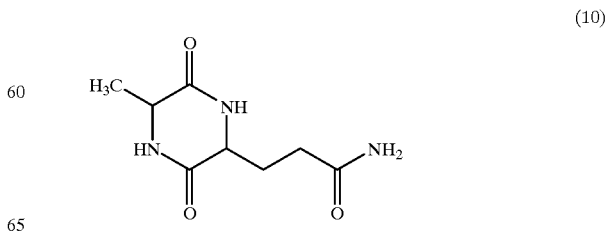

What is claimed is:

1. A method of synthesizing a diketopiperazines of the following formula:

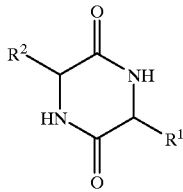

wherein:

$R^1$ is —$CH_2COR^3$, or —$CH_2CH_2COR^3$;

$R^2$ is the side chain of an amino acid selected from the group consisting of glycine, alanine, valine, leucine, isoleucine, serine, threonine, aspartic acid, asparagine, glutamic acid, glutamine, lysine, hydroxylysine, histidine, arginine, phenylalanine, tyrosine, tryptophan, thyroxine, cysteine, methionine, norvaline and ornithine;

$R^3$ is —OH, —$NH_2$, —$OR^4$, —$NHR^4$, or —$NR^4R^4$; and each $R^4$ is independently an alkyl, aryl, alkylaryl, or arylalkyl, the method comprising:

(a) reacting a first amino acid selected from the group consisting of glycine, alanine, valine, leucine, isoleucine, serine, threonine, aspartic acid, asparagine, glutamic acid, glutamine, lysine, hydroxylysine, histidine, arginine, phenylalanine, tyrosine, tryptophan, thyroxine, cysteine, methionine, norvaline and ornithine, with a second amino acid derivative having one of the following formulas:

$NH_2CH(CH_2COOR^5)COOH$ or $NH_2CH(CH_2CH_2COOR^5)COOH$, wherein R5 is benzyl, under conditions effective to form a dipeptide; and, (b) cyclizing the dipeptide at a temperature of between 80° C. and 180° C. in a neutral solvent to form a diketopiperazine having the formula;

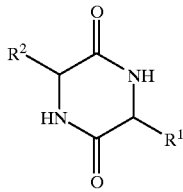

wherein:

$R^6$ is —$CH_2COOR^5$, or —$CH_2CH_2COOR^5$; and (c) hydrogenating the diketopiperazine to remove the $R^5$ group and form a diketopiperazine having the formula:

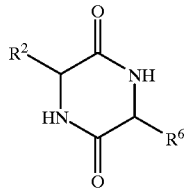

wherein:

$R^1$ is —$CH_2COOH$, or —$CH_2CH_2COOH$; and, $R^2$ is the side chain of an amino acid selected from the group consisting of glycine, alanine, valine, leucine, isoleucine, serine, threonine, aspartic acid, asparagine, glutamic acid, glutamine, lysine, hydroxylysine, histidine, arginine, phenylalanine, tyrosine, tryptophan, thyroxine, cysteine, methionine, norvaline and ornithine.

2. The method of claim 1 wherein the first amino acid is alanine.

3. The method of claim 1 wherein the first amino acid is protected with one or more protecting groups.

4. The method of claim 1 wherein the amino group or α-carboxyl of the second amino acid derivative is protected with a protecting group.

5. The method of claim 1 wherein the neutral solvent comprises butan-2-ol and toluene.

6. The method of claim 1 wherein hydrogenating step (c) is conducted using a palladium on carbon catalyst.

7. The method of claim 1 further comprising derivatizing the compound formed in step (c) at the carboxylic acid of $R^1$ to form a derivative selected from the group consisting of an amide and an ester.

8. The method of claim 1, wherein the first amino acid is attached to a solid support and wherein the dipeptide is removed from the solid support prior to the cyclizing step (b).

* * * * *